United States Patent [19]
Archer et al.

[11] Patent Number: 5,007,988
[45] Date of Patent: Apr. 16, 1991

[54] METHOD FOR DETERMINING THE CONCENTRATION OF A PLURALITY OF COMBUSTIBLE GASES IN A STREAM

[75] Inventors: David H. Archer, Ross Township; Mohammed M. Ahmed, Wilkins Township, both of Allegheny County, Pa.

[73] Assignee: Westinghouse Electric Corp., Pittsburgh, Pa.

[21] Appl. No.: 95,382

[22] Filed: Sep. 8, 1987

[51] Int. Cl.⁵ .............................................. B01D 59/40
[52] U.S. Cl. .............................. 204/153.18; 204/1 S; 204/424; 204/425; 204/426; 204/427; 204/428; 204/429
[58] Field of Search ................. 204/1 S, 1 T, 424–429

[56] References Cited

U.S. PATENT DOCUMENTS

| | | | |
|---|---|---|---|
| 3,819,499 | 6/1974 | Hoogeveen et al. | 204/195 |
| 3,865,707 | 2/1975 | Sayles | 204/195 S |
| 3,907,657 | 9/1975 | Heijne et al. | 205/195 S |
| 4,057,478 | 11/1977 | Bruckenstein et al. | 204/195 P |
| 4,128,458 | 12/1978 | Obiaya | 204/1 T |
| 4,158,166 | 6/1979 | Isenberg | 324/29 |
| 4,380,400 | 4/1983 | Searle | 374/37 |
| 4,462,872 | 7/1984 | Nelson | 204/1 T |
| 4,478,704 | 10/1984 | Miyoshi et al. | 204/412 |
| 4,496,433 | 1/1985 | Annino et al. | 204/1 T |
| 4,545,889 | 10/1985 | Franx | 204/406 |
| 4,547,281 | 10/1985 | Wang et al. | 204/406 |
| 4,576,705 | 3/1986 | Kondo et al. | 204/424 |
| 4,663,017 | 5/1987 | Ross | 204/427 |

*Primary Examiner*—R. L. Andrews
*Attorney, Agent, or Firm*—D. C. Abeles

[57] ABSTRACT

A method for determining the concentration of a plurality of combustible gases in a gas stream comprises providing an electrochemical cell apparatus that includes an electrochemical cell in which a cavity is formed having a diffusion limiting port forming the entrance to the cavity. The cell has a process side in flow communication with a portion of the gas stream flowing into the cavity through the port, and a reference side in flow communication with a reference gas. The process side and the reference side of the electrochemical cell are separated by an electrolyte. The potential difference across the cell is adjusted to create a steady state electrical current flow. A number of the following current flow measurements are obtained, wherein the number of current flow measurements equals the number of combustible gases in the gas stream: determining the steady state current flowing through the electrolyte, and determining the surge of current flowing through the electrolyte after the flow of current is interrupted and then restored, by interrupting the current for a time period, restoring the flow of current and measuring the surge of current until the current attains its steady state value. The total pressure of the gases in the gas stream is measured, and the total pressure and the current flow measurements are converted into an indication of the concentration of each of the combustible gases in the gas stream.

13 Claims, 1 Drawing Sheet

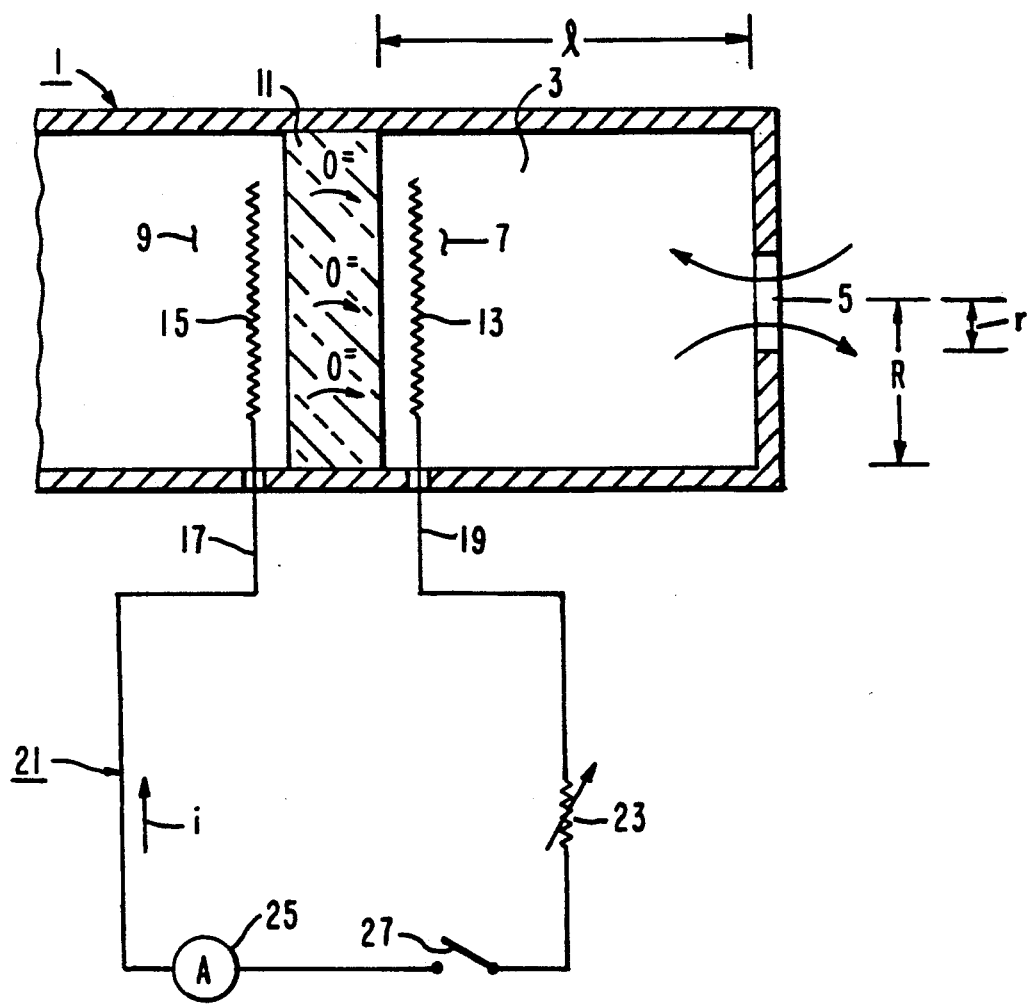

METHOD FOR DETERMINING THE CONCENTRATION OF A PLURALITY OF COMBUSTIBLE GASES IN A STREAM

BACKGROUND OF THE INVENTION

The invention relates to a method for determining the concentration of a plurality of combustible gases in a gas stream.

Current methods of operating oxygen analyzers enable the determination of the total quantity of combustible gases, such as hydrogen, carbon monoxide and methane, in a gas stream. The steady state electrical current flowing through an electrochemical cell is an indication of the quantity of the combustible gases flowing into the cell cavity from the gas stream, because the electrical current is related to the quantity of oxygen ions flowing from the reference gas through the electrochemical cell from the reference side of the electrochemical cell to the process side of the electrochemical cell and into the cell cavity to consume the combustible gases. These methods, however, do not provide the relative quantities of the combustible gases in the gas stream.

Applicants' have disclosed an oxygen analyzer of a type that can be used in the method of the present invention in their U.S. patent application Ser. No. 021,846, filed Mar. 4, 1987, (W.E. 53,198) entitled "Oxygen Analyzer" and assigned to Westinghouse Electric Corporation, the assignee of the present invention. The application is herein incorporated by reference.

Accordingly, it is an object of the present invention to develop a method for determining the concentration of each of the combustible gases in a gas stream.

SUMMARY OF THE INVENTION

The method of the invention enables one to determine the concentration of each of a plurality of combustible gases in a gas stream. An electrochemical cell apparatus is provided that includes an electrochemical cell in which a cavity is formed having a diffusion limiting port forming the entrance to the cavity. The electrochemical cell has a process side in flow communication with a portion of the gas stream flowing into the cavity through the diffusion limiting port, and a reference side in flow communication with a reference gas. The process side and the reference side of the electrochemical cell are separated by an electrolyte. The potential difference across the electrochemical cell is adjusted to create a steady state electrical current flow whereby the flow of oxygen ions from the reference side of the electrochemical cell through the electrolyte to the process side of the electrochemical cell is equal to that required to just consume the flow of combustible gases from the gas stream through the diffusion limiting port into the cell cavity. A number of the following electrical current flow measurements are then obtained, wherein the number of electrical current flow measurements is equal to the number of combustible gases in the gas stream: determining the value of the steady state electrical current flowing through the electrolyte, and determining the surge of electrical current flowing through the electrolyte, over and above the steady state electrical current flow, after the flow of electrical current is interrupted and then restored, by interrupting the electrical current flowing through the electrolyte for a time period, t, after the time period, t, restoring the flow of electrical current through the electrolyte, and measuring the surge of electrical current flowing through the electrolyte over and above the steady state electrical current flow until the electrical current flow attains its steady state value. The total pressure of the gases in the gas stream is determined, and the total pressure and the electrical current flow measurements are converted into an indication of the concentration of each of the combustible gases in the gas stream.

Preferably, the electrical current flow measurements are converted into an indication of the partial pressures of the combustible gases in the gas stream, and the concentration of each of the combustible gases in the gas stream is determined by dividing the partial pressures of each of the combustible gases by the total pressure of the gas stream.

More preferably, the partial pressures of the combustible gases in the gas stream are determined by solving the appropriate equations from the following equations, depending upon the value of t for which the measurement of i, and/or Q was obtained:

$$i = (F*k*A)*[(h\ G1*D\ G1*P^s\ G1) + \ldots + (h\ Gn*D\ Gn*P^s\ Gn)];$$

and, for $x=1$ to $x=n+1$:

$$Qx = [(V*F)/(R*T)]*[(h\ Gy*P^s\ Gy) + (h\ Gy*P^s\ Gy*(1-e^{(-k*D\ Gy*A*tx)}))]$$

wherein

V is volume of the electrochemical cell cavity;

F is Faraday's number;

R is the universal gas constant;

T is the absolute temperature of the gas within the cell cavity;

h Gy is the number of electrons transferred in the half cell equation when combustible gas Gy is reacted with oxygen ions;

$P^s$ Gy is the partial pressure of combustible gas Gy in the gas stream;

$k = (2*\pi*R^2)/[(2*r*l) + R^2]$, wherein

R is the radius of the electrochemical cell;

l is the difference between the length L and the radius R of the electrochemical cell; and r is the radius of the diffusion limiting port;

D Gy is the diffusivity of gas Gy in a mixture of combustible gases G1 through Gn having a composition approximating that of the n combustible gases in the cell cavity;

A is the area of the diffusion limiting port, or $\pi*r^2$, wherein r is the radius of the diffusion limiting port; and tx is the time period for which the electrical current flowing through the electrolyte was interrupted.

An object of the present invention is to enable one to determine the concentration of each of the combustible gases in a gas stream.

BRIEF DESCRIPTION OF THE DRAWING

Other objects and advantages of the present invention will become readily apparent upon reference to the accompanying description when taken in conjunction with the following drawings wherein:

FIGURE 1 is a schematic view of an electrochemical cell that can be used in the method of the subject invention.

DETAILED DESCRIPTION OF THE PREFERRED EMBODIMENTS

The subject invention is a method for determining the concentration of each of a plurality of combustible gases in a gas stream.

Referring to the drawing, an electrochemical cell 1, typical of the type that can be used in the method of the subject invention, is schematically illustrated in FIG. 1. Such an electrochemical cell 1 includes a cavity 3, with a diffusion limiting port 5 forming the entrance to the cavity 3. The electrochemical cell 1 is substantially cylindrical and has a length L and a circular cross-section of radius R. The size of the diffusion limiting port 5 is determined according to engineering principles such that the countercurrent diffusion flow of the various combustible gases, typically hydrogen, carbon monoxide and methane, and of the corresponding combustion products, water vapor and carbon dioxide, can be balanced by the stoichiometric oxygen ion flow through the solid electrolyte of the electrochemical cell 1. The cavity 3 further includes a process side 7 in flow communication with the portion of the gas stream flowing into the cavity 3 through the diffusion limiting port 5 and a reference side 9 in flow communication with a reference gas.

The electrochemical cell 1 is preferably formed of a ceramic material and an electrolyte 11, such as an oxide, that is capable of conducting oxygen ions. Suitable oxides include zirconium oxide, cesium oxide and thorium oxide.

An electrode 13 is attached to the process side 7 of the cell 1 and an electrode 15 is attached to the reference side 9 of the cell 1. Leads 17 and 19, attached to the electrodes 13 and 15, respectively, form part of an electrical circuit 21. The electrical circuit 21 further includes a variable resistor 23, ammeter 25 and switch 27.

The electrochemical cell 1 can be used to measure the concentration of combustible gases in a gas stream. Under reducing conditions in the gas stream, when the switch 27 is closed, the combustible gases diffuse from the gas stream through the diffusion limiting port 5 into the cavity 3 of the electrochemical cell 1. Concurrently, the difference in the partial pressure of oxygen between the reference gas and the gas stream causes oxygen ions to diffuse from the reference gas through the electrolyte 11 toward the lower oxygen partial pressure of the gas stream in the cavity 3 of the electrochemical cell 1 and react with the combustible gases in the cell cavity to form the combustion products, water and carbon dioxide. A potential difference is created between the electrodes 13 and 15 which causes an electrical current to flow between the electrodes 13 and 15, the strength of which can be measured by the ammeter 25.

An external voltage, based on the current carrying capacity of the reference electrode 15 of the electrochemical cell 1 and the concentration range of the gases to be analyzed, is applied to the electrodes 13 and 15 initially to excite the cell 1. The anode electrode is the process side electrode 13 and the cathode electrode is the reference side electrode 15. The reaction at the cathode is:

$$O_2 + 4e^- \rightarrow 2O_2^{--}$$

and the reactions at the anode are, if the combustible gases include hydrogen and carbon monoxide:

$$CO + O^{--} \rightarrow 2e^- + CO_2, \text{ and}$$

$$H_2 + O^{--} \rightarrow 2e^- + H_2O.$$

The combustion products diffuse back to the gas stream from the cavity 3 through the diffusion limiting port 5.

In order to determine the concentration of each of the combustible gases in the gas stream, a number of the following electrical current flow measurements are obtained, wherein the number of electrical current flow measurements is equal to the number of combustible gases in the gas stream. One such electrical current flow measurement is the value of the steady state electrical current flowing through the electrolyte 11. Other such electrical current flow measurements are the surge of electrical current flowing through the electrolyte 11, over and above the steady state electrical current flow, after the flow of electrical current is interrupted and then restored, until the time at which the electrical current flow attains its steady state value.

In order to create and measure the steady state electrical current, i, flowing through the electrolyte 11, the switch 27 is closed and the current flowing through the electrolyte 11 is adjusted, as for example through the variable resistor 23, so that the potential difference across the electrochemical cell 1 corresponds to that developed when the diffusion of oxygen ions from the reference side 9 of the electrochemical cell 1 through the electrolyte 11 to the process side 7 of the electrochemical cell 1 and into the cell cavity 3 equals the diffusion rate of the combustible gases from the combustible gas stream through the diffusion limiting port 5 into the cavity 3 of the electrochemical cell 1. The ammeter 25 registers the strength of the resulting steady state electrical current, i.

In order to measure a current surge, Q, the switch 27 is opened for a preselected period of time, t, thus interrupting the flow of electrical current through the electrolyte 11. The switch 27 is then closed and the resulting surge of electrical current, Q, over and above the steady state electrical current, is recorded from the ammeter 25 as a function of the time after the restoration of electrical current flow until the electrical current flow attains its steady state value.

The total pressure of the gases in the gas stream is measured, and the total pressure of the gas stream, and the electrical current flow measurements, are converted into an indication of the concentration of each of the combustible gases in the gas stream.

Preferably, the electrical current flow measurements are converted into an indication of the partial pressures of the combustible gases in the gas stream, and the concentration of each of the combustible gases in the gas stream is determined by dividing the partial pressures of each of the combustible gases by the total pressure of the gas stream.

The electrical current flow measurements can be converted into an indication of the partial pressures of the combustible gases in the gas stream from relationships described hereinbelow:

If a potential difference is maintained across the electrochemical cell 1 so that the diffusion of oxygen ions from the reference side 9 of the electrochemical cell 1 through the electrolyte 11 to the process side 7 of the electrochemical cell 1 is equal to the diffusion rate of combustible gases from the gas stream through the diffusion limiting port 5 into the cavity 3 of the electrochemical cell 1, the current flow, i, represents both the oxygen ion flow through the electrolyte 11 and the flow of combustible gases through the diffusion limiting port 5 into the cell cavity 3 as follows:

$$i = F * h \, O_2 * d \, O_2, \text{ or} \qquad \text{(equation 1)}$$

-continued $$i = F * \left[ \sum_{x=1}^{x=n} (h\ Gx * d\ Gx) \right], \text{wherein} \quad \text{(equation 2)}$$

h $O_2$ is 4, the number of electrons transferred in the half cell equation:

$$O_2 + 4e^- \rightarrow 2O^{--}$$

d $O_2$ is the diffusion rate of oxygen ions through the electrolyte 11;
F is Faraday's number;
G1 through Gn are the n combustible gases in the gas stream;
h Gx is the number of electrons transferred in the half cell equation:

$$Gx + O^{--} \rightarrow; \text{and}$$

d Gx is the diffusion rate of the gas Gx into the cell cavity 3.

If the combustible gases are hydrogen, methane and carbon monoxide, equation 2 becomes:

$$i = F * [(h\ H_2 * d\ H_2) + (h\ CH_4 * d\ CH_4) + (h\ CO * d\ CO)], \text{wherein} \quad \text{(equation 2A)}$$

h $H_2$ is 2, the number of electrons transferred in the half cell equation:

$$H_2 + O^{--} \rightarrow 2e^- + H_2O$$

h $CH_4$ is 8, the number of electrons transferred in the half cell equation:

$$CH_4 + 4O^{--} \rightarrow 8e^- + CO_2 + 2H_2O$$

h CO is 2, the number of electrons transferred in the half cell equation:

$$CO + O^{--} \rightarrow 2e^- + CO_2$$

d $H_2$ is the diffusion rate of hydrogen into the cell cavity 3;
d $CH_4$ is the diffusion rate of methane into the cell cavity 3; and
d CO is the diffusion rate of carbon monoxide into the cell cavity 3.

Substituting 2, 8 and 2 for h $H_2$, h $CH_4$ and h CO in equation 2 respectively, gives:

$$i = F * [(2 * d\ H_2) + (8 * d\ CH_4) + (2 * d\ CO)] \quad \text{(equation 2B)}$$

And, when the combustible gases are hydrogen and carbon monoxide only, equation 2B becomes:

$$i = F * [(2 * d\ H_2) + (2 * d\ CO)] \quad \text{(equation 2C)}$$

If the concentration of a gas Gx within the cell cavity 3 is zero, as is the case at steady state when the combustible gases are reacted with oxygen ions at the same rate at which the combustible gases diffuse into the cell cavity 3, the diffusion rate, d, of a gas Gx from the gas stream through the diffusion limiting port 5 into the cell cavity 3 is related to the partial pressure of the gas Gx in the gas stream (or the concentration of the gas Gx in the gas stream), and can be represented by:

$$d\ Gx = k * D\ Gx * A * P^s\ Gx, \text{wherein} \quad \text{(equation 3)}$$

D Gx is the diffusivity of the gas x in a mixture of the combustible gases having a composition approximating that of the gases in the gas stream under the temperature and pressure conditions of the cell cavity 3;
A is the area of the diffusion limiting port 5, or $\pi * r^2$, wherein r is the radius of the diffusion limiting port 5;
$P^s$ Gx is the partial pressure of the gas Gx in the gas stream; and
$k = (2 * \pi * R^2) / [(2 * r * l) + R^2]$, wherein
R is the radius of the electrochemical cell 1;
l is the difference between the length L and the radius R of the electrochemical cell 1; and
r is the radius of the diffusion limiting port 5.

Thus, d Gx of equation 3 can be substituted for d Gx of equation 2 as follows:

$$i = F * k * A * \left[ \sum_{x=1}^{x=n} (h\ Gx * D\ Gx * P^s\ Gx) \right] \quad \text{(equation 4)}$$

And, substituting equation 3 for d in equation 2B, $$i = F * k * A * [(2 * D\ H_2 * P^s\ H_2) + (8 * D\ CH_4 * P^s\ CH_4) + (2 * D\ CO * P^s\ CO)] \quad \text{(equation 4A)}$$

And, substituting equation 3 for d in equation 2C, $$i = F * k * A * [(2 * D\ H_2 * P^s\ H_2) + (2 * D\ CO * P^s\ CO)] \quad \text{(equation 4B)}$$

If the flow of electrical current, i, through the electrolyte 11 is interrupted for a time, t, the oxygen ion flow from the reference side 9 to the process side 7 of the electrochemical cell 1 will be interrupted, and combustible gases flowing into the cell cavity 3 will accumulate within the cell cavity 3 because of the lack of available oxygen ions with which to react. Once the flow of electrical current through the electrolyte 11 is resumed, a surge of oxygen ions will flow from the reference side 9 of the electrochemical cell 1 through the electrolyte 11 to the process side 7 of the electrochemical cell 1 as the oxygen ions react with the combustible gases that have accumulated within the cell cavity 3 during the time that the electrical current, and oxygen ion flow through the electrolyte 11, was interrupted. A surge of electrical current, in excess of the steady state current, will occur as the oxygen ions flow through the electrolyte 11 to react with the accumulated combustible gases within the cell cavity 3. The integral of the electrical current surge over the time period from electrical current flow restoration until the electrical current flow attains its steady state value, can be represented by the relationship:

$$\int i\, dt = [(V * F)/(R * T)] * \left[ \sum_{x=1}^{x=n} (h\ Gx * P^c\ Gx) \right], \text{wherein} \quad \text{(equation 5)}$$

$\int i\, dt$, hereinafter represented as Q, is the integral of the electrical current surge over the time period from electrical current flow restoration until the electrical current flow attains its steady state value;
V is the volume of the cavity 3 of the electrochemical cell 1;
R is the universal gas constant;
T is the absolute temperature of the gas within the cell cavity 3; and
$P^c$ Gx is the partial pressure of the gas Gx in the cell cavity 3.

Thus, when the combustion gases are hydrogen, methane and carbon monoxide, and 2, 8, and 2 are substituted for h H2, h CH4 and h CO, respectively, equation 5 becomes:

$$Q = [(V^*F)/(R^*T)]^*[(2^*P^c H_2) + (8^*P^c CH_4) + (2^*P^c CO)] \quad \text{(equation 5A)}$$

And, when the combustion gases are hydrogen and carbon monoxide, equation 5 becomes:

$$Q = [(V^*F)/(R^*T)]^*[(2^* P^c H_2) + (2^* P^c CO)] \quad \text{(equation 5B)}$$

Thus, if the electrical current surge is measured and integrated, after various time periods of electrical current interruption, the concentration of the combustible gases in the gas stream can be determined as follows:

If the flow of electrical current through the electrolyte 11 is interrupted for a sufficient length of time so that the partial pressure of the gas Gx in the cell cavity 3, $P^c$ Gx, equals the partial pressure of the gas Gx in the gas stream, $P^s$ Gx, then the quantity of the gas Gx, $n^c$ Gx in the cell cavity 3 can be related to the partial pressure of the gas Gx in the gas stream, $P^s$ Gx, by the Ideal Gas Law:

$$P^c Gx = P^s Gx = (R^* T^* n^c Gx)/V, \text{ wherein} \quad \text{(equation 6)}$$

R is the universal gas constant.

Thus, if the electrical current flow through the electrolyte 11 is interrupted for a time period long enough for the partial pressure all of the combustible gases in the cell cavity 3 to reach the same partial pressures as the gases have in the gas stream, $$Q = [(V^*F)/(R^*T)] * \left[ \sum_{x=1}^{x=n} (d\, Gx^* P^s Gx) \right] \quad \text{(equation 7)}$$

Similarly, when the time period of electric current interruption is sufficient for the hydrogen, methane and carbon monoxide to reach the same partial pressure within the cell cavity 3 as in the gas stream, equation 5A becomes:

$$Q = [(V^*F)/(R^*T)]^*[(2^*P^s H_2) + (8^*P^s CH_4) + 2^*P^s CO] \quad \text{(equation 7A)}$$

and equation 5B becomes:

$$Q = [(V^*F)/(R^*T)]^*[(2^* P^s H_2) + (2^* P^s CO)] \quad \text{(equation 7B)}$$

However, if the flow of electrical current through the electrolyte 11 is interrupted for a time period less than that required for the partial pressure of the gas Gx in the gas stream to equal the partial pressure of the gas Gx within the cell cavity 3, the partial pressure of the gas Gx in the gas stream can be related to the concentration of the gas Gx within the cell cavity 3 by the relationship:

$$n^c Gx = [(P^s Gx^* V)/(R^*T)]^*[1 - e(-k^*D\, Gx^*A^*t)] \quad \text{(equation 8)}$$

or $$P^c Gx = (P^s Gx)^*[1 - e(-k^*D\, Gx^*A^*t)] \quad \text{(equation 8A)}$$

Thus, if the time period, t, of electrical current interruption is not long enough for any of the combustible gases in the gas stream to reach equilibrium between the gas stream and the cell cavity 3, equation 8A can be substituted for $P^c$ of equation 5, and the surge of electrical current measured after the electrical current flow is interrupted and then restored, until the electrical current flow attains its steady state value, is related to the partial pressures of the gases in the gas stream as follows:

$$Q = [(V^*F)/(R^*T)] * \left( \sum_{x=1}^{x=n} h\, Gx^* P^s Gx^* (1 - e^{(-k^*D\, Gx^*A^*t)}) \right) \quad \text{(equation 9)}$$

However, if the time period, t, of electrical current interruption is long enough for some, but not all, of the combustible gases in the gas stream to reach equilibrium between the gas stream and the cell cavity 3, the expression: h Gx* $P^s$ Gx from equation 6 is used to represent those gases Gx that have reached equilibrium between the gas stream and the cell cavity 3, and the expression: h Gx* $P^s$ Gx* $(1-e^{(-k^*D\, Gx^*A^*t)})$ from equation 9 is used to represent those gases Gx which have not reached equilibrium between the gas stream and the cell cavity 3. Thus, the series of equations which describe the relationship between the surge of electrical current, Q, and the partial pressures of the combustible gases in the gas stream is represented by the following general equation, wherein x is a number of from 1 to n+1 and y is a number of from 1 to n:

$$Qx = [(V^*F)/(R^*T)] * \left[ \sum_{y=1}^{y=x-1} (h\, Gy^* P^s Gy) + \sum_{y=x}^{y=n} (h\, Gy^* P^s Gy^* (1 - e^{(-k^*D\, Gy^*A^*tx)})) \right] \quad \text{(equation 10)}$$

In order to determine the partial pressures of n combustible gases in a gas stream, one only need obtain a number of measurements of i and/or Q, wherein the number of measurements is equal to the number of combustible gases in the gas stream, and depending on the values of t, for which the measurements were obtained, solve the corresponding equations:

$$i = (F^*k^*A) * [(h\, G1^* D\, G1^* P^s G1) + \ldots + (h\, Gn^* D\, Gn^* P^s Gn)];$$

$$Q^1 = [(V^*F)/(R^*T)] * [(h\, G1^* P^s G1^* (1 - e\,(-k^*D\, G1^*A^*t1))) + (h\, G2^* P^s G2^* (1 - e(-k^*D\, G2^*A^*t1))) + \ldots + (h\, Gn^* P^s Gn^* (1 - e\,(-k^*D\, Gn^*A^*t1)))];$$

$$Q^2 = [(V^*F)/(R^*T)] * [(h\, G1^* P^s G1 + (h\, G2^* P^s G2^* (1 - e(-k^*D\, G2^*A^*t2)) + \ldots + (h\, Gn^* P^s Gn^* (1 - e(-k^*D\, Gn^*A^*t2)))];$$

$$Q^3 = [(V^*F)/(R^*T)] * [(h\, G1^* P^s G1) + (h\, G2^* P^s G2) + (h\, G3^* P^s G3^* (1 - e(-k^*D\, G3^*A^*t3)) + \ldots + (h\, Gn^* (1 - e(-k^*D\, Gn^*A^*t3)))];$$

. . .

$$Qn = [(V^*F)/(R^*T)] * [(h\, G1^* P^s G1) + \ldots + (h\, Gn - 1^* P^s Gn - 1) + (h\, Gn^* P^s Gn^* (1 - e^{(-k^*D\, Gn^*A^*tn)}))]; \text{ and}$$

-continued $$Q_n + 1 = [(V^*F)/(R^*T)] * [(h\ G1^* \ P^s\ G1) + \ldots + (h\ G_n^* \ P^s\ G_n)].$$

If there are two combustible gases, such as hydrogen and carbon monoxide, in the gas stream, the concentration of those gases in the gas stream can be determined by measuring the steady state electrical current i and surge of electrical current, Q, after a time period of current interruption, t. If time, t, is sufficient for the hydrogen and the carbon monoxide to reach the same partial pressures within the cell cavity 3 as they have in the gas stream, i.e., $P^cGx = P^sGx$, then the following relationships can be used to determine the concentrations of the hydrogen and carbon monoxide in the gas stream.

$$i = (F^*k^*A)*[(2^*D\ H_2^*P^s\ H_2 + 2^*D\ CO^*P^s\ CO)] \quad \text{(equation 4A)}$$

and $$Q = [(V^*F)/(R^*T)]*[(2^*P^s\ H_2) + (2^*P^s\ CO)] \quad \text{(equation 7A)}$$

Equations 4A and 7A can be simplified to the following equations and solved for the two unknowns, namely: (1) $P^s\ H_2$ and (2) $P_s\ CO$.

$$P^s H_2 = [[i/(2^*F^*k^*A)] - [(D\ CO^*Q^*R^*T)/(2^*F^*V)]]/(D\ H_2 - D\ CO)$$

$$P^s CO = [(Q^*R^*T)/(2^*V^*F)] - [[(i/(2^*F^*k^*A)) - [(D\ CO^*Q^*R^*T)/(2^*F^*V)]]/(D\ H_2 - D\ CO)] \quad \text{(equation 11)}$$

The molar concentration of hydrogen and carbon monoxide in the gas stream can then be calculated by dividing their respective partial pressures, $P^s\ H_2$ and $P^s\ CO$, by the total pressure of the gas stream.

Further, it will be readily understood by one of ordinary skill in the art that if the surge of current, Q, is measured after the electrical current flow is interrupted for a time period, t1, which is not long enough for the hydrogen or carbon monoxide to reach the same concentration within the cell cavity 3 as in the gas stream, the following equation can be used as one of the equations to determine the partial pressures of hydrogen and carbon monoxide within the gas stream:

$$Q1 = [(V^*F)/(R^*T)]*[(2^*\ P^s\ H_2^*(1 - e^{(-k^*D\ H2^*A^*t1)})) + (2^*\ P^s\ CO^*(1 - e(-k^*D\ CO^*A^*t1)))];$$

and if the surge of electrical current, Q, is measured after the electrical current is interrupted for a time period, t2, which is sufficiently long for the hydrogen to reach the same concentration within the cell cavity 3 as in the gas stream, but is not long enough for the carbon monoxide to reach the same concentration within the cell cavity 3 as in the gas stream, the following equation can be used as one of the equations to determine the partial pressures of hydrogen and carbon monoxide within the gas stream:

$$Q2 = [(V^*F)/(R^*T)]*[(2^*\ P^s\ H_2) + (2^*\ P_s\ CO^*(1 - e(-k^*D\ CO^*A^*t2)))].$$

Similarly, if three combustible gases, such as hydrogen, methane and carbon monoxide, are present in the gas stream, the concentration of those gases in the gas stream can be determined by making any three of the following five types of measurements: the steady state electrical current, i; and surge of electrical current, Q, after a time period of electrical current interruption t1, that is not sufficient for any of the gases to reach equilibrium between the gas stream and the cell cavity 3; t2, that is sufficient for hydrogen only to reach equilibrium between the gas stream and the cell cavity 3; t3, that is sufficient for hydrogen and methane, but not carbon monoxide, to reach equilibrium between the gas stream and the cell cavity 3; and t4, sufficient for the three gases to reach equilibrium between the gas stream and the cell cavity 3. The corresponding three of the following equations would then be solved for $P^s\ H_2$, $P^s\ CH_4$, and $P^s\ CO$:

$$i = (F^*k^*A) * [(2^*\ D\ H_2^*\ P^s\ H_2) + \quad \text{(equation 4A)}$$
$$(8^*\ D\ CH_4^*\ P^s\ CH_4) + (2^*\ D\ CO^*\ P^s\ CO)];$$

$$Q^1 = [(V^*F)/(R^*T)] * [(2^*\ P^s\ H_2^* (1 - e(-k^*D\ H2^*A^*t1))) + (8^*\ P^s\ CH_4^* (1 - e(-k^*D\ CH4^*A^*t1))) + (2^*\ P^s\ CO^* (1 - e(-k^*D\ CO^*A^*t1)))];$$

$$Q^2 = [(V^*F)/(R^*T)] * [(2^*\ P^s\ H_2) + (8^*\ P^s\ CH_4^* (1 - e^{(-k^*D\ CH4^*A^*t2)})) + (2^*\ P^s\ CO^* (1 - e(-k^*D\ CO^*A^*t2)))];$$

$$Q^3 = [(V^*F)/(R^*T)] * [(2^*\ P^s\ H_2) + (8^*\ P^s\ CH_4) + (2^*\ P^s\ CO^* (1 - e(-k^*D\ CO^*A^*t3)))]; \text{ and}$$

$$Q^4 = [(V^*F)/(R^*T)] * [(2^*\ P^s\ H_2) + \quad \text{(equation 7A)}$$
$$(8^*\ P^s\ CH_4) + (2^*\ P^s\ CO)].$$

Thus, the method of the invention enables one to determine the concentration of each of the combustible gases in a gas stream.

What is claimed is:

1. A method for determining the concentration of a plurality of combustible gases in a gas stream comprising the steps of:
   (a) providing an electrochemical cell apparatus including a generally cylindrical electrochemical cell formed of a ceramic material in which a cavity is formed having a diffusion limiting port forming the entrance to said cavity, and having a process side in flow communication with a portion of said gas stream flowing into said cavity through said diffusion limiting port, a reference side in fluid flow communication with a reference gas, and an electrolyte separating said process side and said reference side of said electrochemical cell;
   (b) adjusting the potential difference across said electrochemical cell to create a steady state electrical current flow whereby the flow of oxygen ions from said reference side of said electrochemical cell through said electrolyte to said process side of said cell is equal to the flow of combustible gases from said gas stream through the diffusion limiting port into said cell cavity;
   (c) obtaining a number of the following electrical current flow measurements, wherein said number of electrical current flow measurements is equal to the number of combustible gases in said gas stream:
      1. determining the value of said steady state electrical current flowing through said electrolyte; and 2. determining the surge of electrical current flowing through said electrolyte after said flow of electrical current is interrupted and then restored, by:

interrupting said electrical current flowing through said electrolyte for a time period, t, after said time period, t, restoring said flow of electrical current through said electrolyte; and measuring the surge of electrical current flowing through said electrolyte over and above said steady state electrical current flow until the electrical current flow attains its steady state value;

(d) determining the total pressure of the gases in said gas stream; and (e) converting said total pressure and said electrical current flow measurements into an indication of the concentration of each of the n combustible gases in said gas stream.

2. The method of claim 1 wherein said electrical current flow measurements are converted into an indication of the partial pressures of said combustible gases in said gas stream, and the concentration of each of said combustible gases in said gas stream is determined by dividing said partial pressures of each of said combustible gases by said total pressure of said gas stream.

3. The method of claim 1 wherein two combustible gases are present in said gas stream.

4. The method of claim 2 wherein two combustible gases are present in said gas stream.

5. The method of claim 4 wherein said partial pressures of said combustible gases in said gas stream are determined by solving any two of the following equations:

$$i = (F*k*A)*[(h\ G1*D\ G1*P^s\ G1) + (h\ G2*D\ G2*P^s\ G2)];$$

$$Q1 = [(V*F)/(R*T)][(h\ G1*P^s\ G1*(1-e^{(-k*D\ G1*A*t1)})) + (h\ G2*P^s\ G2*(1-e(-k*D\ G2*A*t1)))];$$

$$Q2 = [(V*F)/(R*T)]*[(h\ G1*P^s\ G1) + (h\ G2*P^s\ G2* (1-e(-k*D\ G2*A*t2)))];\ \text{and}$$

$$Q3 = [(V*F)/(R*T)]*[(h\ G1*P^s\ G1) + (h\ G2*P^s\ G2)]$$

wherein;

V is volume of said electrochemical cell cavity;

F is Faraday's number;

R is the universal gas constant;

T is the absolute temperature of said portion of said gas stream within said cell cavity;

h G1 is the number of electrons transferred in the half cell equation when combustible gas 1 is reacted with oxygen ions;

h G2 is the number of electrons transferred in the half cell equation when combustible gas 2 is reacted with oxygen ions;

$P^s$ G1 is the partial pressure of gas 1 in said gas stream;

$P^s$ G2 is the partial pressure of gas 2 in said gas stream;

$k = (2*\pi R^2)/[(2*r*l) + R^2]$, wherein

R is the radius of said electrochemical cell;

l is the difference between the length L and the radius R of said electrochemical cell; and r is the radius of said diffusion limiting port;

D G1 is the diffusivity of combustible gas 1 in a mixture of combustible gases 1 and 2 having a composition approximating that of said combustible gases in said cell cavity;

D G2 is the diffusivity of combustible gas 2 in a mixture of combustible gases 1 and 2 having a composition approximating that of said combustible gases in said cell cavity;

A is the area of said diffusion limiting port, or $*r^2$, wherein r is the radius of said diffusion limiting port;

t1 is a time period, less than that necessary for the combustible gases G1 and G2 to reach equilibrium between said gas stream and said cell cavity, for which the electrical current flowing through said electrolyte was interrupted; and t2 is a time period, less than that necessary for the combustible gas G2 to reach equilibrium between said gas stream and said cell cavity, but greater than that necessary for combustible gas G1 to reach equilibrium between said gas stream and said cell cavity, for which the electrical current flowing through said electrolyte was interrupted.

6. The method of claim 5 wherein said first combustible gas is hydrogen, said second combustible gas is carbon monoxide, h $H_2$ is 2, h CO is 2 and said equations are:

$$i = (F*k*A)*[(2*D\ H_2*P^s\ H_2) + (2*D\ CO*P^s\ CO)];$$

$$Q1 = [(V*F)/(R*T)]*[(2*P^s\ H_2*(1-e(-k*D\ H_2*A*t1))) + (2*P^s\ CO*(1-e(-k*D\ CO*A*t1)))];$$

$$Q2 = [(V*F)/(R*T)]*[(2*P^s\ H_2) + (2*P^s\ CO*(1-e(-k*D\ CO*A*t2)));\ \text{and}$$

$$Q3 = [(V*F)/(R*T)]*[(2*P^s\ H_2) + (2*P^s\ CO)].$$

7. The method of claim 1 wherein three combustible gases are present in said gas stream.

8. The method of claim 2 wherein three combustible gases are present in said gas stream.

9. The method of claim 8 wherein said partial pressures of said combustible gases in said gas stream are determined by solving any three of the following equations:

$$i = (F*k*A) * [(h\ G1*D\ G1*P^s\ G1) +$$
$$(h\ G2*D\ G2*P^s\ G2) + (h\ G3*D\ G3*P^s\ G3)];$$

$$Q^1 = [(V*F)/(R*T)] * [(h\ G1*P^sG1*(1-e^{(-k*D\ G1*A*t1)})) +$$
$$(h\ G2*P^s\ G2*(1-e(-k*D\ G2*A*t1))) +$$
$$(h\ G3*P^s\ G3*(1-e(-k*D\ G3*A*t1)))];$$

$$Q^2 = [(V*F)/(R*T)] * [(h\ G1*P^s\ G1) +$$
$$(h\ G2*P^s\ G2*(1-e(-k*D\ G2*A*t2))) +$$
$$(h\ G3*P^s\ G3*(1-e(-k*D\ G3*A*t2)))];$$

$$Q^3 = [(V*F)/(R*T)].*[(h\ G1*P^s\ G1) +$$
$$(h\ G2*P^s\ G2) + (h\ G3*P^s\ G3*(1-e(-k*D\ G3*A*t3)))];\ \text{and}$$

$$Q^4 = [(V*F)/(R*T)] * [(h\ G1*P^s\ G1) +$$
$$(h\ G2*P^s\ G2) + (h\ G3*P^s\ G3)]$$

wherein;

V is volume of said electrochemical cell cavity;

F is Faraday's number;

R is the universal gas constant;

T is the absolute temperature of said portion of said gas stream within said cell cavity;

h G1 is the number of electrons transferred in the half cell equation when combustible gas 1 is reacted with oxygen ions;

h G2 is the number of electron red in the half cell equation when combustible gas 2 is reacted with oxygen ions;

h G3 is the number of electrons transferred in the half cell equation when combustible gas 3 is reacted with oxygen ions;

$P^s$ G1 is the partial pressure of combustible gas 1 in said gas stream;

$P^s$ G2 is the partial pressure of combustible gas 2 in said gas stream;

$P^s$ G3 is the partial pressure of combustible gas 3 in said gas stream;

$k = (2*\pi*R^2)/[(w*r*l)+R^2]$, wherein

R is the radius of said electrochemical cell;

l is the difference between the length L and the radius R of said electrochemical cell; and r is the radius of said diffusion limiting port;

D G1 is the diffusivity of combustible gas 1 in a mixture of combustible gases 1, 2 and 3 having a composition approximating that of said combustible gases in said cell cavity;

D G2 is the diffusivity of combustible gas 2 in a mixture of combustible gases 1, 2 and 3 having a composition approximating that of said combustible gases in said cell cavity;

D G3 is the diffusivity of combustible gas 3 in a mixture of combustible gases 1, 2 and 3 having a composition approximating that of said combustible gases in said cell cavity;

A is the area of said diffusion limiting port, or $\pi*r^2$, wherein r is the radius of said diffusion limiting port;

t1 is a time period, less than that necessary for the combustible gases G1, G2 and G3 to reach equilibrium between said gas stream and said cell cavity, for which the electrical current flowing through said electrolyte was interrupted;

t2 is a time period, less than that necessary for the combustible gases G2 and G3 to reach equilibrium between said gas stream and said cell cavity, but greater than that necessary for combustible gas G1 to reach equilibrium between said gas stream and said cell cavity, for which the electrical current flowing through said electrolyte was interrupted; and t3 is a time period, less than that necessary for the combustible gas G3 to reach equilibrium between said gas stream and said cell cavity, but greater than that necessary for combustible gases G1 and G2 to reach equilibrium between said gas stream and said cell cavity, for which the electrical current flowing through said electrolyte was interrupted.

10. The method of claim 9 wherein said first combustible gas is hydrogen, said second combustible gas is methane, said third combustible gas is carbon monoxide, h $H_2$ is 2, h $CH_4$ is 8, h CO is 2 and said equations are:

$i = (F*k*A) * [(2* D\ H_2* P^s H_2) +$ $(8* D\ CH_4* P^s CH_4) + (2* D\ CO* P^s CO)];$ $Q^1 = [(V*F)/(R*T)] * [(2* P^s H_2* (1 - e(-k*D\ H_2*A*t1))) +$ $(8* P^s CH_4* (1 - e(-k*D\ CH_4*A*t1))) +$ $(2* P^s CO* (1 - e(-k*D\ CO*A*t1)))];$ $Q^2 = [(V*F)/(R*T)] * [(2* P^s H_2) +$ $(8* P^s CH_4* (1 - e(-k*D\ CH_4*A*t2))) +$ $(2* P^s CO* (1 - e(-k*D\ CO*A*t2)))];$ $Q^3 = [(V*F)/(R*T)] * [(2* P^s H_2) +$ $(8* P^s CH_4) + (2* P^s CO* (1 - e(-k*D\ CO*A*t3)))];$ and $Q^4 = [(V*F)/(R*T)] * [(2* P^s H_2) + (8* P^s CH_4) + (2* P^s CO)].$ 11. The method of claim 1 wherein n combustible gases are present in said gas stream.

12. The method of claim 2 wherein n combustible gases are present in said gas stream.

13. The method of claim 3 wherein said partial pressures of said combustible gases in said gas stream are determined by solving any n of the following equations:

$i = (F*k*A) * [(h\ G1* D\ G1* P^s G1) + \ldots +$ $(h\ Gn* D\ Gn* P^s Gn)];$ and, for $x = 1$ to $x = n + 1$:

$Qx = [(V*F)/(R*T)] * \left[ \sum_{y=1}^{y=x-1} (h\ Gy* P^s Gy) + \right.$ $\left. \sum_{y=x}^{y=n} (h\ Gy* P^s Gy* (1 - e(-k*D\ Gy*A*tx))) \right]$ wherein;

V is volume of said electrochemical cell cavity;

F is Faraday's number;

R is the universal gas constant;

T is the absolute temperature of the gas within said cell cavity;

h Gy is the number of electrons transferred in the half cell equation when combustible gas Gy is reacted with oxygen ions;

$P^s$ Gy is the partial pressure of combustible gas Gy in said gas stream;

$k = (2*\pi*R^2)/[(2*r*l)+R^2]$, wherein

R is the radius of said electrochemical cell;

l is the difference between the length L and the radius R of said electrochemical cell; and r is the radius of said diffusion limiting port;

D Gy is the diffusivity of gas Gy in a mixture of combustible gases G1 through Gn having a composition approximating that of said n combustible gases in said cell cavity;

A is the area of said diffusion limiting port, or $\pi*r^2$, wherein r is the radius of said diffusion limiting port; and tx is the time period for which the electrical current flowing through said electrolyte was interrupted.

* * * * *